(12) United States Patent
Hammarlund et al.

(10) Patent No.: US 10,359,417 B2
(45) Date of Patent: **\*Jul. 23, 2019**

(54) PORTABLE SAMPLING DEVICE AND METHOD FOR DETECTION OF BIOMARKERS IN EXHALED BREATH

(71) Applicant: Sensa Bues AB, Huddinge (SE)

(72) Inventors: Bo Hammarlund, Sollentuna (SE); Olof Beck, Saltsjöö-Boo (SE)

(73) Assignee: Sensa Bues AB, Huddinge (SE)

( * ) Notice: Subject to any disclaimer, the term of this patent is extended or adjusted under 35 U.S.C. 154(b) by 17 days.

This patent is subject to a terminal disclaimer.

(21) Appl. No.: 14/383,846

(22) PCT Filed: Mar. 8, 2013

(86) PCT No.: PCT/EP2013/054789
§ 371 (c)(1),
(2) Date: Sep. 8, 2014

(87) PCT Pub. No.: WO2013/132085
PCT Pub. Date: Sep. 12, 2013

(65) Prior Publication Data
US 2015/0033824 A1 Feb. 5, 2015

Related U.S. Application Data

(60) Provisional application No. 61/608,326, filed on Mar. 8, 2012.

(51) Int. Cl.
*A61B 5/097* (2006.01)
*A61B 5/08* (2006.01)
*G01N 33/497* (2006.01)

(52) U.S. Cl.
CPC ........... *G01N 33/497* (2013.01); *A61B 5/082* (2013.01); *A61B 5/097* (2013.01); *G01N 2033/4975* (2013.01)

(58) Field of Classification Search
CPC .................................................... G01N 33/497
See application file for complete search history.

(56) References Cited

U.S. PATENT DOCUMENTS

| 3,316,904 A | 5/1967 | Wall |
| 4,292,978 A | 10/1981 | Guth |

(Continued)

FOREIGN PATENT DOCUMENTS

| DE | 19718924 A1 * | 10/1998 | ........... G01N 33/497 |
| DE | 10137161 A1 * | 2/2003 | ............. B01D 39/00 |

(Continued)

OTHER PUBLICATIONS

Office Action dated Apr. 22, 2015 in connection with related Russian Application No. 201391293/31, filed Nov. 21, 2013.

(Continued)

*Primary Examiner* — Herbert K Roberts
(74) *Attorney, Agent, or Firm* — Downs Rachlin Martin PLLC

(57) ABSTRACT

A portable method and sampling device for collecting aerosols comprising biomarkers from exhaled breath of a subject for further sensor based analysis. The sampling device (41) comprising a housing (406) comprising at least one inlet (407) and at least one outlet (408) for the exhaled breath to exit through, and a sampling membrane arranged in the housing. The sampling membrane is arranged to collect the aerosols from said exhaled breath.

23 Claims, 6 Drawing Sheets

(56) References Cited

U.S. PATENT DOCUMENTS

| | | | |
|---|---|---|---|
| 4,327,741 A * | 5/1982 | Watson | A61B 5/097 482/13 |
| 4,809,810 A | 3/1989 | Elfman | |
| 4,900,514 A * | 2/1990 | Fuller | G01N 33/4972 285/328 |
| 5,042,501 A | 8/1991 | Kenny et al. | |
| 5,195,527 A | 3/1993 | Hicks | |
| 5,369,977 A * | 12/1994 | Rhodes | G01N 33/4972 422/83 |
| 5,465,728 A | 11/1995 | Phillips | |
| 5,467,776 A | 11/1995 | Hamilton | |
| 5,478,377 A | 12/1995 | Scavnicky et al. | |
| 5,518,002 A | 5/1996 | Wolf | |
| 5,721,102 A | 2/1998 | Vo-Dinh | |
| 5,834,626 A | 11/1998 | De Castro | |
| 6,097,480 A | 8/2000 | Kaplan | |
| 6,209,541 B1 | 4/2001 | Wallace | |
| 6,623,997 B2 | 9/2003 | Farquharson et al. | |
| 7,285,246 B1 | 10/2007 | Martin | |
| 7,450,227 B2 | 11/2008 | Dwight et al. | |
| 8,368,883 B2 | 2/2013 | Palmskog et al. | |
| 8,705,029 B2 | 4/2014 | Palmskog | |
| 2002/0095078 A1 | 7/2002 | Mannheimer et al. | |
| 2002/0177232 A1 | 11/2002 | Melker et al. | |
| 2003/0028120 A1 | 2/2003 | Mault et al. | |
| 2004/0045889 A1 | 3/2004 | Harkonen | |
| 2004/0236244 A1 | 11/2004 | Allen | |
| 2005/0048660 A1 | 3/2005 | Bearer | |
| 2005/0051719 A1 | 3/2005 | Miller et al. | |
| 2005/0065446 A1 | 3/2005 | Talton | |
| 2005/0137491 A1 | 6/2005 | Paz et al. | |
| 2005/0233459 A1 | 10/2005 | Melker et al. | |
| 2006/0021302 A1 | 2/2006 | Bernard | |
| 2006/0038990 A1 | 2/2006 | Habib et al. | |
| 2006/0078467 A1 | 4/2006 | Stock | |
| 2006/0084182 A1 | 4/2006 | Farquharson et al. | |
| 2006/0119853 A1 | 6/2006 | Baumberg et al. | |
| 2006/0153740 A1 | 7/2006 | Sultan et al. | |
| 2006/0160134 A1 | 7/2006 | Melker | |
| 2006/0266353 A1 | 11/2006 | Yamada et al. | |
| 2007/0023627 A1 | 2/2007 | Finch et al. | |
| 2007/0156211 A1 | 7/2007 | Ferren et al. | |
| 2007/0185405 A1 | 8/2007 | Altobelli | |
| 2007/0224128 A1 | 9/2007 | Dennis et al. | |
| 2007/0252077 A1 | 11/2007 | Shoji | |
| 2007/0258894 A1 | 11/2007 | Melker et al. | |
| 2008/0183388 A1 | 7/2008 | Goodrich | |
| 2010/0036272 A1 * | 2/2010 | Mace | A61B 5/083 600/531 |
| 2010/0083838 A1 * | 4/2010 | Togashi | B01D 39/1623 96/10 |
| 2010/0264042 A1 * | 10/2010 | Varney | G01N 33/497 205/783 |
| 2010/0297635 A1 * | 11/2010 | Olin | A61B 5/411 435/6.11 |
| 2011/0053173 A1 | 3/2011 | Hood | |
| 2011/0098590 A1 | 4/2011 | Garbutt | |
| 2012/0212735 A1 | 8/2012 | Palmskog et al. | |
| 2012/0302907 A1 | 11/2012 | Palmskog et al. | |
| 2013/0066223 A1 | 3/2013 | Beck et al. | |
| 2013/0128260 A1 | 5/2013 | Palmskog et al. | |
| 2014/0065602 A1 | 3/2014 | Milton | |
| 2014/0366609 A1 | 12/2014 | Beck et al. | |
| 2016/0034809 A1 | 2/2016 | Trenholm | |

FOREIGN PATENT DOCUMENTS

| | | |
|---|---|---|
| EP | 0997733 | 5/2000 |
| EP | 2518499 A1 | 10/2012 |
| JP | H04507204 | 12/1992 |
| JP | 07120462 | 5/1995 |
| JP | 08510948 | 11/1996 |
| JP | 2001-505660 A | 4/2001 |
| JP | 2004-301749 A | 10/2004 |
| JP | 2007-525670 A | 9/2007 |
| JP | 2008102048 | 1/2008 |
| JP | 2009-047593 A | 3/2009 |
| WO | 0184112 | 11/2001 |
| WO | 3057521 | 7/2003 |
| WO | 2005098429 | 10/2005 |
| WO | 2009030957 | 3/2009 |
| WO | 2009045163 | 4/2009 |
| WO | 2011029888 | 3/2011 |

OTHER PUBLICATIONS

Response to Office Action dated May 14, 2015, in connection with related U.S. Appl. No. 13/394,609, filed May 29, 2012.
Final Office Action dated Jun. 19, 2015, in connection with related U.S. Appl. No. 13/394,609, filed May 29, 2012.
Response to Final Office Action dated Aug. 19, 2015, in connection with related U.S. Appl. No. 13/394,609, filed May 29, 2012.
Advisory Action dated Sep. 2, 2015, in connection with related U.S. Appl. No. 13/394,609, filed May 29, 2012.
Final Office Action dated Apr. 28, 2015, in connection with related U.S. Appl. No. 13/416,956, filed Mar. 9, 2012.
Response to Final Office Action dated Jun. 29, 2015, in connection with related U.S. Appl. No. 13/416,956, filed Mar. 9, 2012.
Advisory Action dated Jul. 24, 2015, in connection with related U.S. Appl. No. 13/416,956, filed Mar. 9, 2012.
Beck, O et al., "Method for determination of methadone in exhaled breath collected from subjects undergoing methadone maintenance treatment," Journal of Chromatography B: Biomedical Sciences & Applications, Elsevier, Amsterdam, NL., Jul. 3, 2010, pp. 2255-2259, vol. 878, No. 24.
Beck, Olof et al., Amphetamines Detected in Exhaled Breath from Drug Addicts: A New Possible Method for Drugs-of-Abuse Testing; Journal of Analytical Toxicology, vol. 34 Jun. 2010; pp. 233-237.
Beck, Olof et al., "Demonstration that methadone is being present in the exhaled breath aerosol fraction", Aug. 3, 2011, Journal of Pharmaceutical and Biomedical Analysis, pp. 1024-1028, ISSN: 0731-7085.
Bernd Sagmuller et al, Application of SERS Spectroscopy to the identification of (3,4-methylenedioxy) Amphetamine in Forensic Samples Utilizing Matrix Stabilized Silver Halides, Oct. 2001, pp. 2066-2071, vol. 126, No. 11, The Analyst, The Royal Society of Chemistry 2001.
Buszewski Boguslaw et al., "Human exhaled air analytics: biomarkers of diseases," Biomedical Chromatography, Jun. 2007, pp. 553-566 & 588, vol. 21, No. 6.
EPO Communication re Personal Consultation with Examiner, dated Dec. 10, 2012, issued in connection with related EP10751947.2.
EPO Communication, Article 94(3) dated Mar. 7, 2013, issued in connection with related EP10751947.2.
EPO Communication, Article 94(3) dated Oct. 23, 2012, issued in connection with related EP10751947.2.
European Search Report dated Jun. 8, 2011, in connection with related EP Application No. 11157565.
Extended European Search Report dated Apr. 11, 2012, in connection with related EP Application No. 12 15 8911.
International Preliminary Report on Patentability dated Oct. 27, 2011, in connection with related PCT/EP2010/063265 filed Sep. 9, 2010.
International Search Report and Written Opinion dated Nov. 19, 2010, for related application PCT/EP2010/063266 filed Sep. 9, 2010, entitled "Drug Detection in Exhaled Breath," Palskog, G et al.
International Search Report dated Nov. 24, 2010, in connection with related PCT/EP2010/063265 filed Sep. 9, 2010.
International Search Report dated Oct. 4, 2013, in connection with related PCT/EP2013/068860, filed Sep. 11, 2013.
Marks, P, "Taking on the drugged and drunk drivers," New Scientist, Reed Business Information, Surrey, GB, vol. 188, No. 2528, Dec. 3, 2005, pp. 28-29.

(56) References Cited

OTHER PUBLICATIONS

Miekisch, W et al., "Assessment of propofol concentrations in human breath and blood by means of HS-SPME-GC-MS," Clinica Chimica Acta, Elsevier BV, Amsterdam, NL, Sep. 1, 2008, pp. 32-37, vol. 395, No. 1-2.
Sagmuller et al., Application of SERS spectroscopy to the identification of (3,4-methylenedioxy)amphetamine in forensic samples utilizing matrix stabilized silver halides, Analyst, Royal Society of Chemistry, GB, vol. 126, No. 11, Nov. 1, 2001, pp. 2066-2071.
Sanchez, C et al., "Determination of Nitroaromatic Compounds in Air Samples at Femtogram Level Using C18 Membrane Sampling and On-line Extraction with LC-MS," Analytical Chemistry, Sep. 1, 2003, pp. 4639-4645, vol. 75, No. 17.
Sulk et al., Surface-Enhanced Raman Scattering Detection of Amphetamine and methamphetamine by Modification with 2-Mercaptonicotinic Acid, Applied Spectroscopy, the Society for Applied Spectroscopy, Baltimore, US, vol. 53, No. 8, Jan. 1, 1999, pp. 954-959.
Written Opinion dated Apr. 11, 2012, in connection with related EP Application No. 12 15 8911.
Written Opinion dated Jun. 8, 2011, in connection with related EP Application No. 11157565.
Written Opinion dated Oct. 4, 2013, in connection with related PCT/EP2013/068860, filed Sep. 11, 2013.
Office Action dated Oct. 21, 2013, in connection with related Japan Application No. Tokugan-2012-528364.
Office Action dated Nov. 14, 2014, in connection with related U.S. Appl. No. 13/394,609, filed May 29, 2012.
Office Action dated Aug. 2, 2013, in connection with related U.S. Appl. No. 13/739,607, filed Jan. 11, 2013.
Response to Office Action dated Dec. 2, 2013, in connection with related U.S. Appl. No. 13/739,607, filed Jan. 11, 2013.
Office Action dated Aug. 13, 2014, in connection with related U.S. Appl. No. 13/416,956, filed Mar. 9, 2012.
Response to Office Action dated Jan. 13, 2015, in connection with related U.S. Appl. No. 13/416,956, filed Mar. 9, 2012.
International Search Report dated Apr. 2, 2012, issued in connection with related PCT/EP2012/054180, filed: Mar. 9, 2012.
Written Opinion dated Apr. 2, 2012, issued in connection with related PCT/EP2012/054180, filed: Mar. 9, 2012.
Periago, J. F. et al.; "Design and evaluation of an exhaled breath sampler for biological monitoring of organic solvents," Journal of Applied Toxicology, vol. 12, No. 2, Apr. 1, 1992; pp. 91-96; ISSN: 0260-437X.
Written Opinion dated Jul. 3, 2014 in connection with related EP14164314.8, filed Sep. 9, 2010.
European Search Report dated Jul. 3, 2014 in connection with related EP14164314.8, filed Sep. 9, 2010.
Zwir-Ferenc, A., et al., Solid Phase Extraction Technique—Trends, Opportunities and Applications; Polish J. of Environ. Stud., vol. 15, No. 5 (2006); pp. 677-690.
Amendment and Response Filed with RCE dated Oct. 28, 2015, in connection with U.S. Appl. No. 13/416,956, filed Mar. 9, 2012.
Office Action dated Dec. 17, 2015, in connection with U.S. Appl. No. 14/222,696, filed Mar. 24, 2014.
RCE and Amendment dated Dec. 21, 2015, in connection with U.S. Appl. No. 13/394,609, filed May 29, 2012.
Office Action dated Jan. 7, 2016, in connection with U.S. Appl. No. 14/427,229, filed Mar. 10, 2015.
Office Action dated Feb. 17, 2016 related to U.S. Appl. No. 13/394,609, filed May 29, 2012, Goran Palmskog.

Office Action dated Feb. 1, 2016 related to U.S. Appl. No. 13/416,956, filed Mar. 9, 2012, Olof Beck.
International Search Report dated May 23, 2013, in connection with related PCT/EP2013/054789, filed Mar. 8, 2013.
Written Opinion dated May 23, 2013, in connection with related PCT/EP2013/054789, filed Mar. 8, 2013.
Fabian, Patricia et al., "Influenza virus in human exhaled breath: an observational study", PLoS One 2008, vol. 3, No. 7, Jul. 16, 2008, p. e2691, XP7921865, ISSN: 1932-6203.
Almstrand, Ann-Charlotte et al: "Airway monitoring by collection and mass spectrometric analysis of exhaled particles", Analytical Chemistry, American Chemical Society, vol. 81, No. 2, Jan. 15, 2009, pp 662-668, XP007915715; ISSN: 0003-2700.
Beck, Olof et al., "Study on the sampling of methadone from exhaled breath", Journal of Analytical Toxicology, vol. 35, No. 5, Jun. 2011, pp. 257-263, XP55045425.
Mutlu G. M., et al., "Collection and analysis of exhaled breath condensate in Humans", American Journal of Respiratory and Critical Care Medicine, American Lung Association, NY, NY, vol. 164, 2001, pp 731-737, XP003012811, ISSN: 1073-449X.
Office Action dated Jul. 28, 2016, in connection with U.S. Appl. No. 14/003,915, filed Feb. 18, 2014, Olof Beck.
Final Office Action dated Aug. 26, 2016, in connection with U.S. Appl. No. 13/416,956, Olof Beck.
Final Office Action dated Aug. 18, 2016, in connection with U.S. Appl. No. 13/394,609, Palmskog et al.
EPO Communication Pursuant to Article 94(3) dated Jan. 11, 2016, in connection with European Application No. 13713094.4.
Chia-Wei Chang et al; "Non-labeled virus detection using inverted triangular Au nano-cavities arrayed as SERS-active substrate", Sensors and Actuators B, vol. 156, No. 1, Apr. 12, 2011; pp. 471-478; XP028222875, ISSN: 0925-4005, DOI: 10.1016/J.SNB.2011.04.0006.
Patrick Dolan et al; "Can we detect influenza?", Proceedings of Spie, vol. 7703, Apr. 5, 2010, p. 77030T, XP55238702, ISSN: 0277-786X, DOI: 10.1117/12.853652.
Seung Min Yoo et al: "Detection of Single Nucleotide Polymorphisms by a Gold Nanowire-on-Film SERS Sensor Coupled with S1 Nuclease Treatment", Chemistry—A European Journal, vol. 17, No. 31, Jul. 25, 2011, pp. 8657-8662, XP55238700, ISSN: 0947-6539, DOI: 10.1002/chem.201003372.
Hsin-Neng Wang et al; "Multiplex detection of breast cancer biomarkers using plasmonic molecular sentinel nanoprobes", Nanotechnology, vol. 20, No. 6, Jan. 14, 2009, p. 65101, XP020153133, ISSN: 0957-4484, DOI: 10.1088/0957-4484/20/6/065101.
Amendment and Response to First Non-Final Office Action dated Oct. 28, 2016, in connection with U.S. Appl. No. 14/003,915, filed Feb. 18, 2014.
Response to Office Action dated Jun. 1, 2016, in connection with U.S. Appl. No. 13/416,956, filed Mar. 9, 2012, Olof Beck.
Amendment and Response to First Non-Final Office Action dated Apr. 18, 2016, in connection with U.S. Appl. No. 14/222,696, Palmskog et al.
Amendment and Response to First Office Action after RCE dated May 17, 2016, in connection with U.S. Appl. No. 13/394,609, Palmskog et al.
Amendment and Response to First Office Action dated Apr. 6, 2016, in connection with U.S. Appl. No. 14/427,229, Beck.
Notice of Allowance dated Apr. 26, 2016, in connection with U.S. Appl. No. 14/427,229, Beck.
Final Office Action dated Jun. 15, 2016, in connection with U.S. Appl. No. 14/222,696, Palmskog, et al.

* cited by examiner

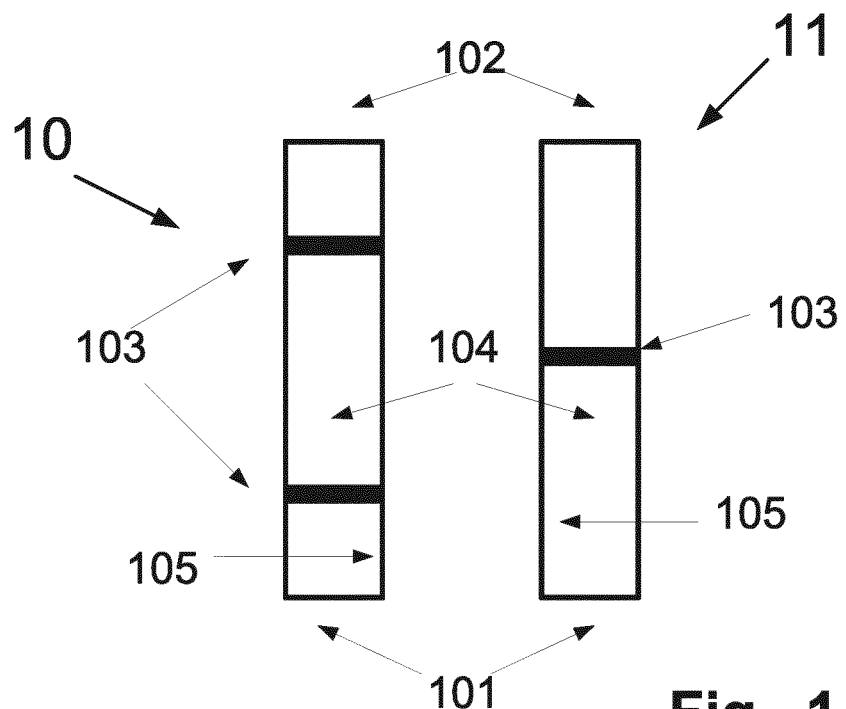
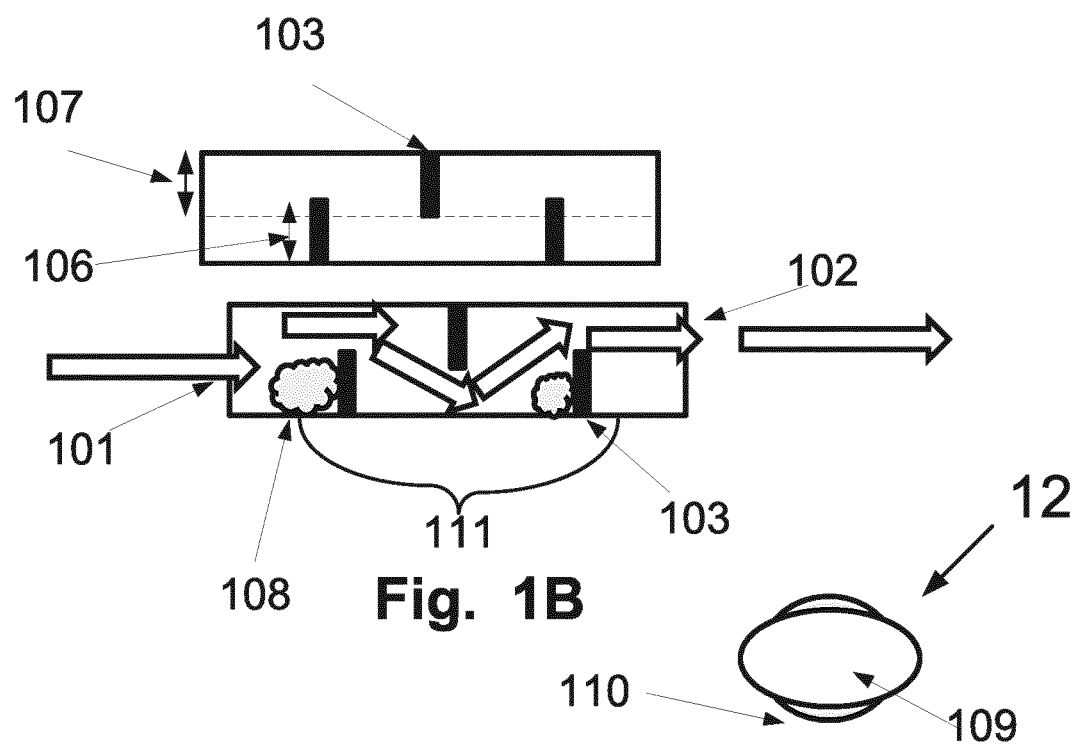
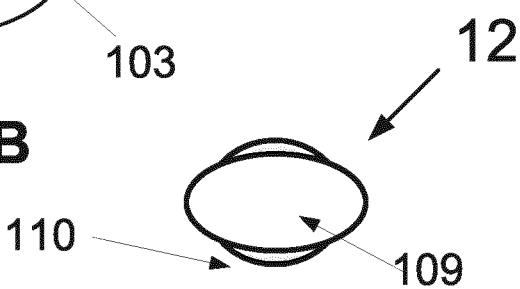

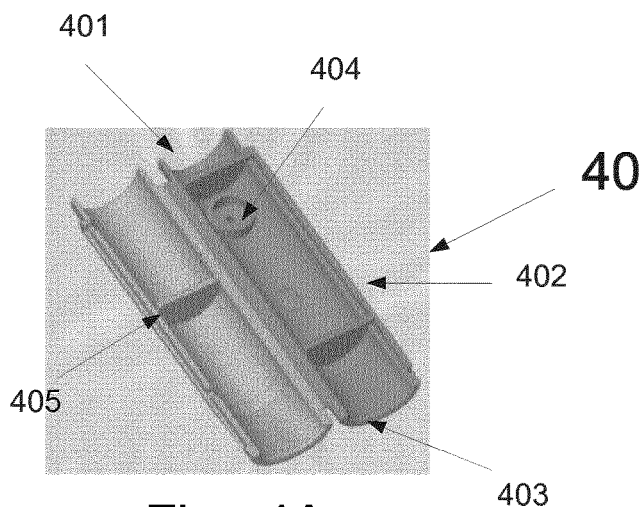
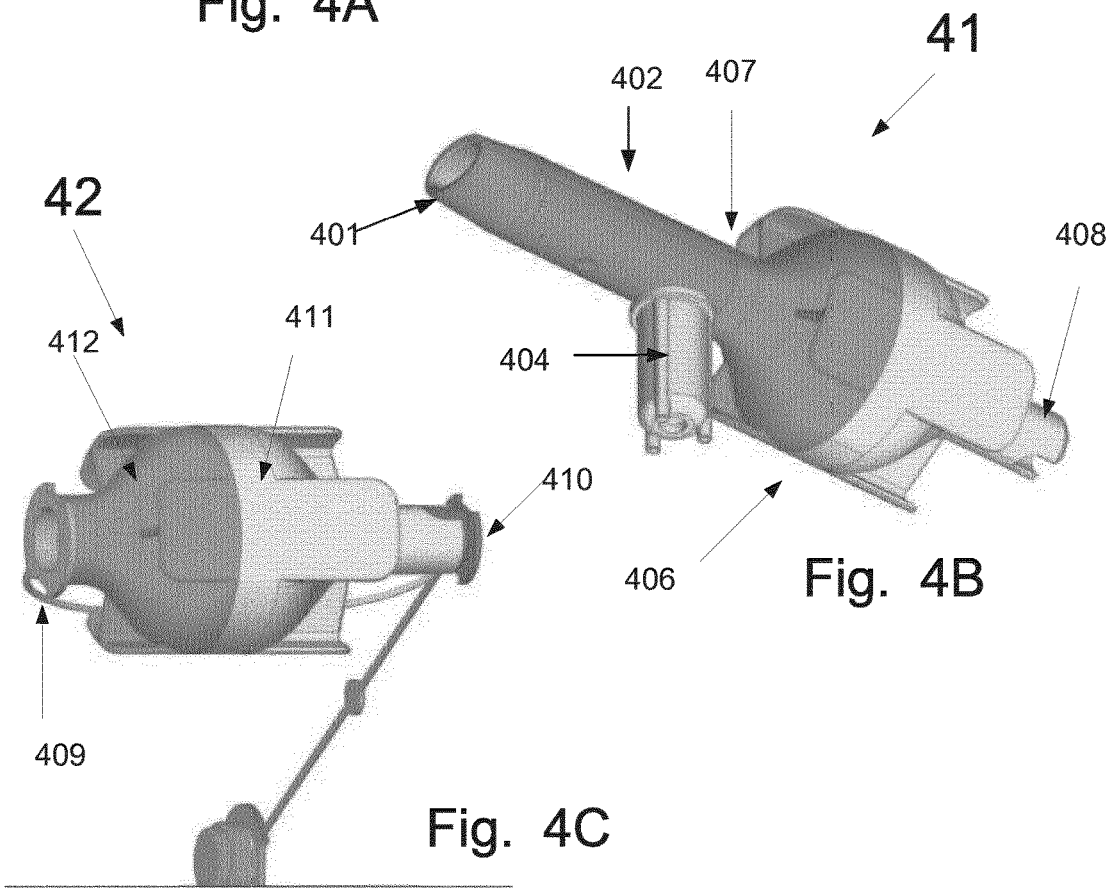

PORTABLE SAMPLING DEVICE AND METHOD FOR DETECTION OF BIOMARKERS IN EXHALED BREATH

FIELD OF THE INVENTION

This invention pertains in general to the field of portable handheld devices, sampling systems and methods for collecting a sample from exhaled breath of a subject, and for detecting the presence (i.e. qualitative) or determining the quantitative amount of at least one biomarker in said exhaled breath. The sampled biomarkers may be analyzed for diagnosis of a medical condition, e.g. a disease or an illness, More particularly the invention relates to such portable handheld sampling devices.

BACKGROUND OF THE INVENTION

There has been an increased interest in biomarkers to be used in methods for diagnosing different medical conditions of patients. Lately, there has been found that some of these biomarkers may be traced in samples from exhaled breath for example by using exhaled breath condensate (EBC) i.e. exhaled water vapour that is condensed by the means of low temperature, where both volatile and non-volatile compounds have been identified. The non-volatiles found in EBC are believed to originate from particles formed within the airways. The collection of exhaled breath condensate (EBC) is connected with a number of serious methodological difficulties such as dilution with water resulting in very low concentrations of the substances of interest, high contamination with substances originating from the oral cavity, high intraindividual coefficient of variation and a very inefficient way to sample the non-volatiles found in EBC. Hence there is a need for better non-invasive methods to detect and monitor adverse health effects of the respiratory system. Non-volatile compounds are transported by aerosol particles that are believed to derive from the respiratory tract lining fluid, lung alveoli or bronchioles.

There is a lack of methods for easy monitoring of the airways and to also allow frequent sampling. Measuring biomarkers in exhaled air is non-invasive and enables repeated sampling which can be useful for early detection of disease as well as monitoring of disease progression and therapy response.

Thus, there is a need to provide a non-invasive based apparatus, system and/or method for detecting the presence (i.e. qualitative) or determining the quantitative amount of at least one biomarker for medical diagnosis of a subject. Particularly, a device and method being easy to use with no or little training, especially a device and method for directly, at the site/on-site, screening a subject for a medical diseases or illnesses would be advantageously. The device and method should have a sensitive for biomarkers high enough to obtain results of a standard that could be used for diagnosis of medical conditions.

Hence, an improved apparatus, system and/or method for at site/on site sampling of biomarkers from a subject is desired. The apparatus, system and/or method should be efficient, non-bulky, user friendly both for operators and the subject.

SUMMARY OF THE INVENTION

Accordingly, examples of the present disclosure preferably seek to mitigate, alleviate or eliminate one or more deficiencies, disadvantages or issues in the art, such as the above-identified, singly or in any combination by providing a system and a method, according to the appended patent claims.

According to one aspect of the disclosure, a portable sampling device for collecting aerosols comprising biomarkers from exhaled breath of a subject for further sensor based analysis is provided. The device comprising a housing comprising at least one inlet and at least one outlet for said exhaled breath to exit through, and a sampling membrane arranged in said housing. The sampling membrane is arranged to collect said aerosols from said exhaled breath.

The exhaled breath volume is not stored in a volume for analysis of the chemical contents of the entire breath volume. Rather, traces of the biomarkers are attached to a sampling membrane. Analysis is not made online of the breath volume, but of the traces in the sampling membrane. The portable sampling device may be sealed and sent further for the analysis. Collection of the traces of biomarkers is made quickly, by exhaling a predetermined volume of breath through the sampling membrane. The obtain results, when using the device are reliable and have a proven robustness. Using the invented biomarker sampling device is far more convenient, quicker and cheaper than any previous breath sample collection methods.

Biomarker compounds exhaled in expired air may be transported by aerosols that may originate from mucus layer and/or respiratory tract lining fluid. Alternatively, compounds may originate from other parts of the airways. Non-volatile compounds may be transferred from the lungs carried by an aerosol, here the non-volatile compounds are biomarkers. The biomarkers are collected on-site/in-situ using a portable sampling device comprising a sampling membrane. The collected samples are to be sent to a laboratory for further analysis. Alternatively, compact on-site analysis may be performed. The analysis is performed using a suitable analyzing method like spectroscopy or preferably mass-spectroscopy or Surface enhanced Raman spectroscopy (SERS).

Since the portable sampling device is small and designed to be easy to handle it may be used by any personnel anywhere on-site.

The housing could be made of any material like, plastic, metal or glass as long as it is possibly to have it sterile or aseptic or to easily clean. The housing could alternatively or in addition be made of a disposable material. In this way the housing may, after being used for sampling, and after the analysis of the collected compounds has been performed, be discarded.

A tubular element having a selective trap section may optionally be used to improve the quality of the test by preventing big particles and/or aggregates and/or saliva and/or mucus to be collected by the sampling membrane.

In some examples of the disclosure, the tubular element is detachable from the housing or the tubular element is an integrated part of said housing.

In some examples of the disclosure, the device further comprises a volume measure unit for determining that a pre-defined volume of the exhaled breath has passed through the sampling membrane. Additionally, in some examples of the device, the volume measure unit comprising a gas volume collecting element, such as a bag, having a volume and wherein a port is arranged downstream a mouthpiece and upstream the sampling membrane and wherein the port is adapted to extract a defined portion of the exhaled breath into said volume measure unit. The volume of the gas volume collecting element is proportional to said pre-defined volume of the exhaled breath.

This is an easy and effective way of determining when a pre-defined volume of exhaled breath has passed through the sampling membrane. The bag is blown up by utilizing the back pressure due to air flow resistance of the sampling membrane.

In some examples of the disclosure, the volume collecting element is a non-elastic bag with a predetermined size.

An elastic bag could be used but a non-elastic bag with a specific volume is easier to blow up and can only hold that specific volume.

In some examples of the disclosure, the sampling membrane is a filter membrane, preferably an electrostatic filter membrane.

In some examples of the disclosure, The filter membrane comprising at least one layer of non-woven filtration media with a specific weight in the range of 23 g/m3 to 500 g/m3, preferably in the range of 150 up to 300 g/m3, and even more preferably in the range of 200 up to 280 g/m3.

In some examples of the disclosure, the filter membrane comprising at least on further layer being a spunbonded carrier with a scrim weight of 10 to 20 g/m3.

One important parameter of a sampling device that is fulfilled by a filter membrane made of fibers is the low pressure drop. To be able to collect exhaled breath samples from most subjects the pressure drop through the system has to be as low as possible. The flow rate of a subject's exhalation depends on some parameters for example the subject's age, mental state (MR, Alzheimer's), medical condition (sepsis, Parkinson's) or other medications like benzodiazepines, opiates, neuroleptics, local anesthetics or intoxicants etc.

In some examples of the disclosure, the filter membrane has a filter surface to be passed by exhaled gas of approximately 800 mm2 and a pressure drop of 36 Pa at 9.5 m/min media velocity.

In some examples of the disclosure, the filter membrane is made of a blend of acrylic fibers and polypropylene fibers.

The acrylic fibers have electrostatic properties while the polypropylene fibers will make the filter structure stronger, for example may the polypropylene fibers give the filter membrane enough support so that requires sizes and shapes can be punched out from the material.

In some examples of the disclosure, the housing may have at least two outlets.

Two outlet will help to prevent a subject to be tested from stopping the air from flowing out of the outlet and thereby preventing enough exhaled breath from passing through the sampling element.

In some examples of the disclosure, the tubular element further comprises an inlet, an outlet in connection with a lumen, at least two baffles, each having a height of at least a length of a radius of the lumen. The baffles are arranged on different sides of the lumen to deny an exhaled breath a straight path through the lumen of the conduit. Primarily aerosols in the exhaled breath are permitted to pass though the tubular element.

In some examples of the disclosure, each baffle may comprise orifices with a size that only permit the aerosols to pass through.

The mass-spectroscopy or SERS are the preferred analyzing methods, since these technologies have a very high selectivity and sensibility of bioanalysis especially with regards to trace analytes in biological samples. The preferable interface for the mass spectroscopy is liquid chromatography.

The sampling membrane may be emptied from collected particles and analyzed by dissolving the collected particles from the exhaled breath in a solvent. The solvent could than be analyzed by the sensor unit. Another method could be to evaporate the content of the sampling membrane onto a SERS surface.

According to a further aspect of the invention, a method of detecting biomarkers from exhaled breath of a subject is disclosed. The method comprises collecting a sample of aerosols in a sampling membrane of a collection device. Extracting a content from the sampling membrane and employing a sensor unit for detecting traces of biomarkers in the content.

In some examples of the disclosure, the method comprises investigating a health status of a subject based on an analysis of the traces of biomarkers.

In some examples of the disclosure, the investigating is used for diagnosing a medical condition of the subject. The method further includes diagnosing the subject based on a measurement signal or result obtained from the sensor unit related to the biomarkers.

In some examples of the disclosure, the method includes measuring a pre-defined fraction of the exhaled breath volume for determining a specific total volume of the exhaled breath passing through the sampling membrane. Terminating the exhalation the exhalation after the specific total volume is determined as having passed through the sampling membrane.

In some examples of the disclosure, the method includes sealing the device before sending it to a lab for extracting the content.

In some examples of the disclosure, the method includes performing on-site analysis. Additionally and/or alternatively, in some examples of the disclosure, the content is extracted from the sampling membrane using a solvent. Additionally and/or alternatively, the solvent with said extracted content may be placed on a surface of the sensor unit and thereafter evaporated. This will leave only the content on the surface to be analyzed.

In some examples of the disclosure, the sampling membrane used in the method may be a filter membrane, preferably an electrostatic filter membrane. Additionally and/or alternatively, the filter membrane may comprise at least one layer of a non-woven filtration media with a specific weight in the range of 23 $g/m^3$ to 500 $g/m^3$, preferably in the range of 150 up to 300 $g/m^3$, and even more preferably in the range of 200 up to 280 $g/m^3$. Additionally and/or alternatively, the filter membrane may comprise at least on further layer being a spunbonded carrier with a scrim weight of 10 to 20 $g/m^3$. Additionally and/or alternatively, the filter membrane may have a filter surface to be passed by exhaled gas of approximately 800 $mm^2$ and a pressure drop of 36 Pa at 9.5 m/min media velocity. Additionally and/or alternatively, the filter membrane may be made of a blend of acrylic fibers and polypropylene fibers.

In some examples of the disclosure, the method utilizing a tubular element connected to an inlet of the collection device for preventing contaminates, such as big particles and/or aggregates and/or saliva and/or mucus, to be collected by the sampling membrane. For example, the tubular element may comprise an inlet and an outlet in connection with a lumen. The tubular element may further comprise at least two baffles positioned in the selective trap section, each having a height of at least a length of a radius of the lumen. Further, the baffles may be arranged on different sides of the lumen to deny an exhaled breath a straight path through the lumen of the conduit, whereby primarily aerosols in the exhaled breath may be permitted to pass though the tubular element.

Known non-volatile biomarker that may be transported by aerosols in exhaled breath is comprised in the list comprising lipids, peptides, nucleotides, prostanoids, proteins, DNA or RNA.

These biomarkers may be used for diagnosis of diseases or illnesses, such as cancer (such as lung cancer), asthma, inflammation, infection (such as tuberculosis) and/or oxidative stress.

Additionally and/or alternatively, content transported by aerosols and trapped or collected in the filter membrane may be pathogens, including virus particles, bacteria, yeast, fungus, disease cells, and the like. These may then be analyzed for diagnosis of diseases or illnesses.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which:

FIG. 1A-C are schematic illustrations showing an example of a tubular element with a mouthpiece section, designed to mainly permit aerosols from exhaled breath from a subject to pass through;

FIG. 4A-C are depicting the portable sampling device at different stages;

DESCRIPTION OF EXAMPLES

Figure 2:
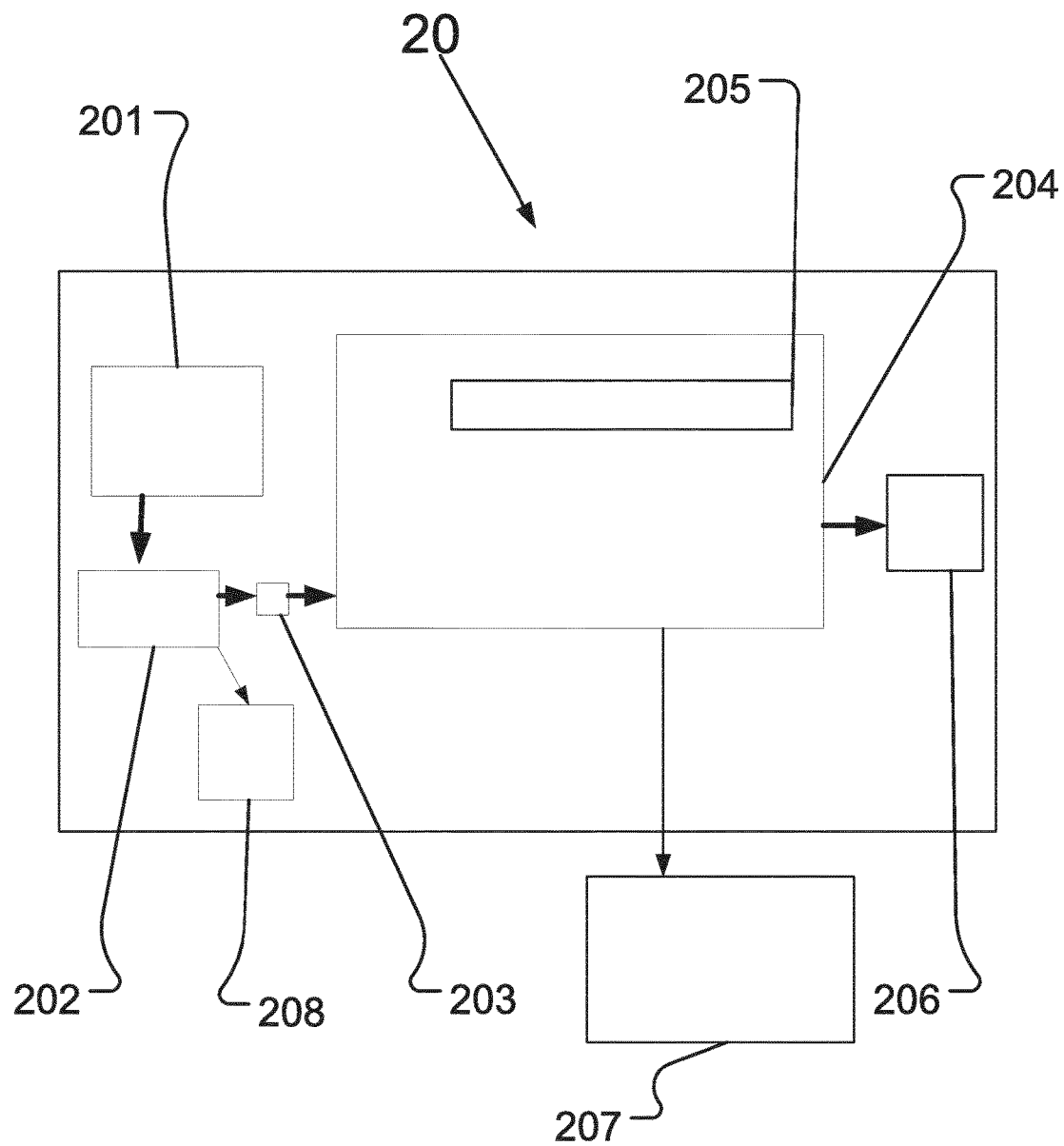
FIG. 2 is a schematic illustration illustrating an example of a portable device configured to collect a sample from exhaled breath of a subject.

Specific examples of the disclosure will now be described with reference to the accompanying drawings. This disclosure may, however, be embodied in many different forms and should not be construed as limited to the examples set forth herein; rather, these examples are provided so that this disclosure will be thorough and complete, and will fully convey the scope of the disclosure to those skilled in the art. The terminology used in the detailed description of the examples illustrated in the accompanying drawings is not intended to be limiting of the disclosure. In the drawings, like numbers refer to like elements.

In an example of the disclosure according to FIG. 1A-C a tubular element with a mouthpiece section and a selective trap section is depicted. The tubular element is designed to permit primarily aerosols to pass through. Hence denying contaminants, such as saliva and/or mucus, and/or larger particles and/or aggregated, to enter the housing and thereby avoiding the membrane to be clogged.

The tubular element is a conduit with a coaxial lumen having transversal baffles. The cross-section of the lumen could have any shape but is preferably circular or oval. In FIG. 1A two complementary cross-section views 10, 11 along the length of a tubular element with a mouthpiece section are shown. The shape of the two parts are close to two half-pipes, wherein both parts comprising open ends 101, 102 which will form an inlet, being a mouthpiece section, and an outlet, when put together. The section between the inlet 101 and outlet 102 is a selective trap section 111. In FIG. 1A, part 10 comprises two transversal baffles 103 and part 11 one. Hence the total number of baffles 103 seated in the lumen 104 in the illustrated example of the tubular element is three. In reality any suitable number of baffles needed to obtain the needed effect could be seated in the lumen of the tubular element. The section with the baffles 103 forms the selective trap section 111.

The transversal baffles 103 may be perpendicular to the inner wall 105 of the lumen 104 (as depicted in FIG. 1A). Alternatively and/or additionally, in some examples the transversal baffles 103 may have any suitable angle relative the inner wall 105 of the lumen 104.

In FIG. 1B a cross-section of the tubular element is depicted from a different view, showing the height of the transversal baffles and the path the exhaled breath must travel from the inlet 101 to the outlet 102. In the upper cross-section view the height 106 of the baffles 103 are shown related to the radius 107 of the lumen. The baffles 103 protrude into the lumen 104 at least a distance being the same as the radius 107. Preferably the height 106 of the baffles 103 should be taller than the length of the radius 107 of the lumen 104. The baffles 103 are in FIG. 2B depicted as perpendicular to the inner wall 105 of the lumen 104. In reality each baffle 103 could have any suitable angle relative the inner wall 105 of the lumen 104 as long as they extend into the lumen the same distance as the radius 107 or longer.

The baffles 103 should be spaced to the passing of aerosols are optimized and at the same time minimizing the amount of contaminants, such as saliva and/or particles and/or aggregates 108, permitted through the tubular element to the outlet 102. Alternatively and/or additionally, in some examples the spacing is depending on the height and/or the angle of the baffles 103.

Further in FIG. 1B, the arrows in the lower cross-section show the travel of exhaled breath and the aerosols through the tubular element. The aerosols will easily travel from the inlet 101 to the outlet 102 while the heavier or larger in size particles or aggregates 108 will be denied by the baffles 103. The tubular element may therefore act as a pre-filter.

Alternatively and/or additionally, in some examples of the disclosure the baffles 103 include orifices sized to mainly permit aerosols to pass through the orifices.

In FIG. 1C the mouthpiece section 12 is depict. The inlet 109 could have any shape but one that has shown to be particularly suitable and comfortable is an oval shape. 110 depict the contours of the tubular section previously described in FIGS. 4 A and B.

In FIG. 2 is a schematic illustration showing an example of a portable device configured to collect a sample from exhaled breath of a subject. Sampling device 20 is configured to collect a sample from exhaled breath of a subject 201. The subject will exhale through a mouthpiece. Optionally, the mouthpiece may be connected to a tubular element 202 being in flow communication with a housing 204 via at least one inlet 203. The mouthpiece and the optional tubular element 202 may be of same size or type as a conventional used for alcohol-test. Additionally and/or alternatively, in some preferred examples, the mouthpiece and the tubular element 202 is configured to mainly permit aerosols to pass through. Even more preferably configured according to the previously described disclosure.

The housing 204 could be made of any suitably material or combinations thereof such as, metal, plastic, glass or ceramics.

The housing 204 comprises a sampling membrane 205 for collecting the non-volatile biomarkers from the exhaled breath. The exhaled breath exits the housing through at least one outlet 206. The portable device is sealed after being used and sent to a laboratory 207 to be analyzed. Analysis of the biomarkers could be performed using a range of methods but preferably methods are Surface enhanced Raman spectroscopy (SERS) or mass-spectroscopy, for example Liquid-chromatography mass-spectroscopy (LCMS).

Alternatively and/or additionally, in some examples the portable sampling device is made to be a disposable product. When designed to be a disposable product the housing as well as the mouthpiece is preferably made of a plastic material.

The sampling device and elements for collecting biomarkers should be kept clean and preferable be aseptic but could also be used sterile.

Alternatively and/or additionally, in some examples of the disclosure a volume measure unit 208 may be used for detecting the amount of exhaled breath from the tested subject. Preferably the volume measure unit 208 comprising a port arranged downstream the mouthpiece section and upstream the sampling membrane 205. Preferably the port is attached to the tubular element. A pre-defined fraction or portion of the exhaled breath will be extracted through the port and used for calculating the amount of exhaled breath passed through the sampling membrane 205. Preferably the volume measure unit 208 is further comprising a gas volume collecting element, preferably a bag, in communication with the port. The gas volume collecting element has a predefined volume when expanded. The volume of exhaled breath passed through the sampling membrane 205 may be proportional to the volume of the bag when full.

Figure 3:
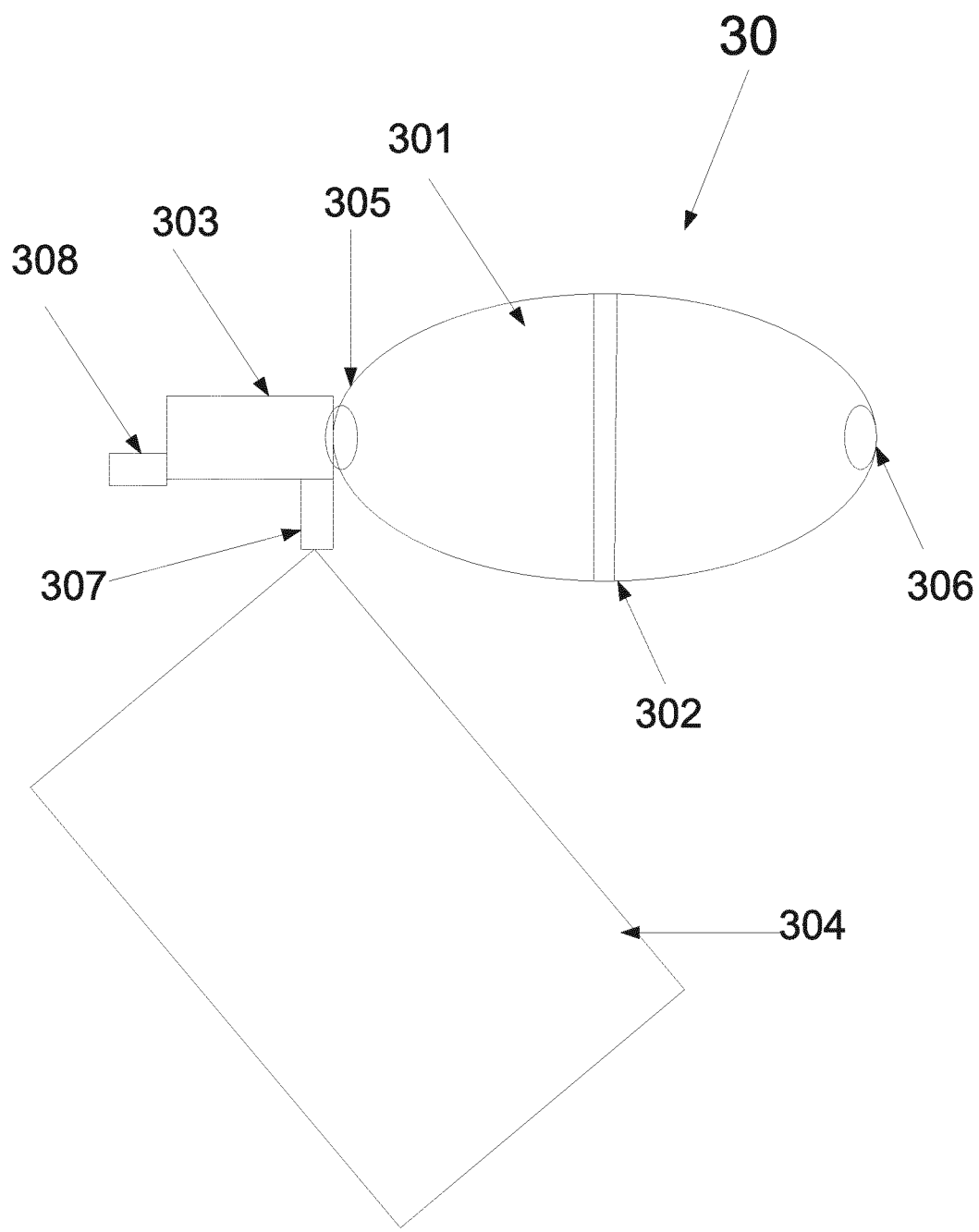
FIG. 3 is an example of a portable sampling device showing a housing with a sampling element being a filter membrane.

In FIG. 3 is an example of a portable sampling device 30 is depicted comprising a housing 301, with a sampling membrane 302, a tubular element 303 with a mouthpiece section 308 and a selective trap section, and a volume measure unit comprising a port 307 and a gas volume collecting element 304. The volume measure unit is used for calculating the volume of exhaled breath passing through the sampling membrane 302.

The sampling membrane could be placed anywhere in the housing 301. Preferably the sampling membrane is fastened to the inner walls of the housing 301. The housing 301 is preferably constructed out of two or more parts, a first part with an inlet 305 and one part with at least one outlet 306.

The mouthpiece section 308 and the optional tubular element 303 is detachable and in fluid communication with the housing 301 via the inlet 305. The tubular element 303 is acting as a pre-filter for filtering out contaminants, such as saliva and/or mucus and/or large particles and/or aggregates, from the exhaled breath, according to what has previously been described. Thus a cleaner filter to be analyzed is obtained which may result in better and more accurate analysis. Other advantages with using a tubular element 303 is the prevention of contamination between subjects and sample.

Alternatively and/or additionally, in some examples the mouthpiece section 308 and tubular element 303 is not detachable but integrated with the first part of the housing 301.

Connected either to the tubular element 303 or between the mouthpiece section 308 and the inlet 305 is a port 307 for extracting a portion or fraction of the exhaled breath from the subject. The extracted exhaled breath is used to blow up a gas volume measuring element 304, such as non-elastic bag or an elastic balloon. In this example a non-elastic bag made of plastic is used since it requires less force to be blown up and will automatically stop when full.

When the bag is full the exhaled breath passing through the filter membrane can be calculated since it will be proportional to volume of the bag. For example, by extracting a tenth of the volume exhaled by the subject, a full two liter bag means that 18 liter has passed through the filter membrane (20 liter exhaled in total).

Additionally, in some examples the port may comprise a one-way valve so that the extracted breath will only enter the bag but not leave.

Alternatively and/or additionally, in some examples the port utilizes the back pressure created by the filter membrane to extract the exhaled breathe through the port 307.

The exhaled breathe will, after flowing through the tubular element 303, travel into the housing 301 and be brought into contact with the sampling membrane, preferably a filter membrane.

The biomarkers being non-volatile compounds conveyed as aerosols in the exhaled breath conveyed is collected by the filter membrane as the exhaled breath is permeated through the filter membrane.

It should be noted that the sampling element 302 being a filter membrane is not to be confused with an electronic or chemical sampling units and/or traps. The sampling element 302 is a physical entity on which the biomarkers are collected. Collection may in different examples be based on various principles, singly or in combination, comprising depositing, catching, fastening, condensing of non-volatile constituents on the sampling element 302.

Using a filter membrane allows for a low pressure drop through the portable system 30 making it easy and comfortable to exhale through it.

In the example depicted in FIG. 3, the filter membrane is placed to block the path for the exhaled breath through the portable system 30. In other examples the filter could be placed along the side of any of the walls of the housing 301.

There are many possibilities for fastening the filter membrane is needed, either by using a separate support structure retaining the filter, which may be an element that is either fastened to the inside walls of the housing 301 or a segment being slide onto a first part of the housing during the assembly before the second part of the housing is mounted.

Alternatively and/or additionally, in some examples the filter membrane is fastened direct onto the inside walls of the housing 301, either by glue or by heat and thereby melting a small part of the edge of the filter membrane.

The second part of the housing is either screwed or slid onto the first part of the housing. The second part comprises at least one outlet 306. Alternatively and/or additionally, in some example the housing 301 comprises at least two outlets 306. This will aid to avoid a subject being tested to block the outlet and thereby blowing up the measuring element 304 with minimum exhaled breath being permeated through the filter membrane.

In an example of the portable device 30 the sampling element 302 is a filter membrane made of synthetic and/or half-synthetic fibers for the exhaled breath to diffuse through.

The filter membrane will have a structure that catches the aerosols and thereby collects the aerosols being exhaled while letting gas pass through. The aerosol particles comprise the non-volatile biomarkers. Preferably the filter membrane is operable to collect the aerosols from the air with a high volumetric capacity while maintaining a low pressure drop across the filter substrate.

Alternatively and/or additionally, in some examples the filter membrane may be an electrostatic filter made of fibers.

Alternatively and/or additionally, in some examples the filter membrane may be of a non-woven polymeric fibrous that may be an electret.

Alternatively and/or additionally, in some examples the filter membrane is a electrostatic filter being preferably a non-woven filter membrane comprising a blend of acrylic fibers and polypropylene fibers. The filter membrane could have a density (sometimes called grade or weight) in the range 23 up to 500 g/m2. But it has been shown that the range 130 up to 300 g/m2 is preferred. Even more preferably is the range 200 up to 280 g/m2.

Alternatively and/or additionally, in some examples the non-woven layer could be attached to at least further layer. Further layers could be used to enhance a filter membrane's physical properties or improve filtration performance. The extra layer could be a carrier, preferably a polypropylene spunbonded carrier. The spunbond carrier may have a scrim weight in the range 10 up to 20 g/m2, preferably 15 g/m2.

For example a three layered filter membrane comprising one non-woven layer with a density of 250 g/m2 and two layers being carriers each with a scrim weight of 15 g/m2 will have a air flow resistance of about 36 Pa at 9.5 m/min media velocity.

Alternatively and/or additionally, in some examples the filter membrane may be corrugated to enhance the filtering area within a given housing volume.

The portable system is configured and adapted to have a sensitive for biomarkers high enough to obtain results of a standard that could be used for diagnosis of medical conditions. Other advantages are that the test can be done anywhere at a low cost and short lead time before obtaining a result. Since no specially trained personnel are needed and the test is does not need to be performed at, for example, a hospital.

Other advantages are that the invented portable sampling system is non-invasive. Even known issues with methods used today such as dilution of the particles (such as EBC) are avoided.

In FIG. 4A-C is one example of the disclosure illustrated at different stages. FIG. 4A depicts a tubular element 40 before being assembled and mounted. 401 shows the mouthpiece section with an inlet, 402 shows the optional tubular element being a selective trap section, 403 shows the outlet, 404 the port for extracting a portion of the exhaled breath and 405 shows the baffles used to obtain the non-straight gas flow path.

FIG. 4B illustrates the device 41 when being ready to be used: 401 shows the mouthpiece section; 402 the tubular section comprising the baffles; 407 is the inlet to the housing 406; 408 shows the outlet from the housing 406; 404 is the port for extracting a portion of the exhaled breath. The illustration does not show the volume measure unit (i.e. the bag) attached to the extraction port 404.

In FIG. 4C is a used sampling device 42. The mouthpiece section and tubular element is detached and plugs 409, 410 are mounted to the inlet 407 and the outlet 408 of the housing 406. This will seal off the housing 406 and the sampling membrane comprised inside. At this stage the portable sampling device 42 is ready to be sent to a laboratory, for example by post. In FIG. 4C it is shown that the housing 406 is made of two parts 411 and 412 mounted together.

Figure 5:
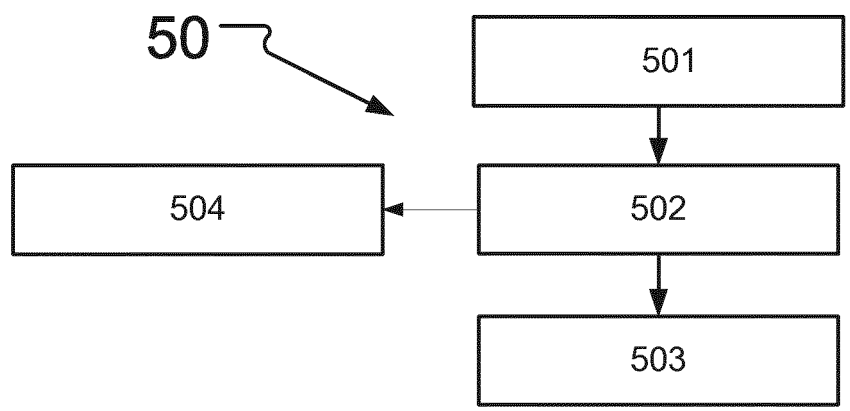
FIG. 5 is a flow-chart illustrating a method for using a portable device configured to collect a sample from exhaled breath of a subject.

FIG. 5 is a flow-chart illustrating a method 50 for using a portable system configured to collecting a sample 502 from exhaled breath from a subject. Briefly, FIG. 5 illustrates detecting the presence and/or determining the quantitative amount 503 of at least one biomarker in a collected sample. The biomarker may be collected attached to an aerosol, being non-volatile particles and/or compounds, from the exhaled breath. The method comprising of: a subject exhaling 501 into the invented portable system; a sampling unit will collect a sample 502 that may comprise biomarkers; the collected sample will be extracted from the sampling membrane and analyzed 503 using mass-spectroscopy or SERS.

With reference to FIG. 5, a subject will exhale 501 in and out; preferably the subject will exhale into the portable device until a specific volume of exhaled breath has been passed through the filter membrane.

Alternatively and/or additionally, in some examples the subject has to exhale either for a certain time or for a fixed number of times such as 1 to 10 times into a portable system. When breathing a fixed number of times each exhale could be set to last for a fixed time.

To measure a specific volume, one preferred method is to use a port between either located on the mouthpiece or between the mouthpiece and the inlet of the housing. A portion of the exhaled breath will be extracted 504 through the port and blow up an element such as a non-elastic bag. Hence when the bag is full, the volume of said bag will be proportional to the volume passed through the filter membrane.

Alternatively and/or additionally, in some examples a bag with elastic properties can be used.

A deep breath is preferred to reach exhaled breath from deep lying lung portions such as the central or the peripheral lung regions.

The exhaled breath will then be collected 502 by the sampling element, i.e. an easy to breathe through filter membrane, suitably for collecting biomarkers before it exits the device. The filter membrane is preferably made of synthetics and/or half synthetics fibers; preferably the filter membrane has electrostatic-properties. Using a filter membrane will create a small, light weighted and easy to use method that can be used everywhere by anyone to sample biomarkers to be used when diagnosing a medical condition of a subject. Since the methods collects the particles directly problems associated with known methods such as EBC are prevented.

After being used, the housing of the sampling system will sealed off by sealing the inlet and the outlet and be sent to a laboratory, whereby the collected compounds in the filter are removed and analyzed 503 using an appropriate analyzing method such as mass-spectroscopy or SERS.

Figure 6:
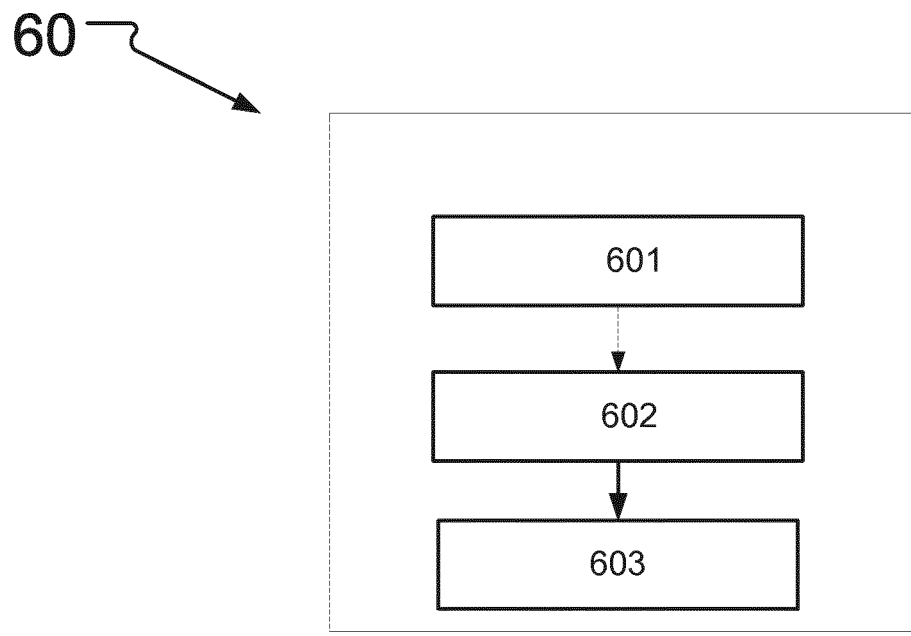
FIG. 6 illustrates a system for detecting the presence or determining the quantitative amount of at least one biomarker in exhaled breath.

FIG. 6 illustrates a system 60 for detecting the presence or determining the quantitative amount of at least one biomarker in exhaled breath. The system comprising a portable sampling device 602 for handheldly collecting a sample from exhaled breathe from a subject 601. The device 602 could be according to any example described herein.

Further, the system 60 comprises a sensor unit 603 for analyzing the collected compounds in the testing device 602. The sensor could be any know type of sensor but preferably mass spectroscopy or SERS. To be able to analyze the collected sample the content of the filter membrane in the device 602 is extracted. This could be done for example by using a solvent to be analyzed using the sensor unit 603. Another method is heating the filter and thereby evaporating the content of the filter for example onto a SERS surface.

Alternatively, the content of the filter is extracted using a solvent. At least a portion of the solvent, comprising the extracted content, is then placed and evaporated on a surface of a sensor unit, such as a SERS surface. Whereafter the content is analyzed using the sensor. This may be performed either on-site or in a lab.

The present disclosure has been described above with reference to specific examples. However, other examples than the above described are equally possible within the scope of the disclosure. Different method steps than those described above, performing the method by hardware or software, may be provided within the scope of the disclosure. The different features and steps of the disclosure may be combined in other combinations than those described. The scope of the disclosure is only limited by the appended patent claims.

The invention claimed is:

1. A method of detecting biomarkers from exhaled breath of a subject, comprising:
   collecting a sample of aerosols from a deep breath reaching exhaled breath from central or peripheral lung regions in a sampling membrane arranged in a handheld and portable collection device, the collection device includes a chamber made from two parts jointed together for the exhaled breath to be exhaled through, wherein the sampling membrane comprises at least two layers, and wherein at least one layer is gas permeable and another layer is an electrostatic non-woven filter, the sampling membrane is arranged transversal to a flow of exhaled breath in the chamber to collect said aerosols from the exhaled breath, and wherein said sampling membrane is configured for a low pressure drop through said handheld and portable collection device for said subject to exhale through said handheld and portable device un-aided, so that said exhaled breath flows unaided from an inlet to an outlet of said device; the device further comprises a detachable tubular element having a lumen in flow connection with the inlet of the collection device; wherein the tubular element is formed by two opposite parts, each part having at least one baffle such that when connected the tubular element comprises at least two baffles arranged on opposite sides of said lumen to provide a non-straight path through the tubular element, said baffles protrude into said lumen at a distance larger than a radius of said lumen; the device further comprises a volume measure unit for determining that a pre-defined volume of said exhaled breath has passed through said sampling membrane, wherein the volume measure unit is connected through a port in the tubular element, and wherein said volume measuring unit is a non-elastic bag with a predetermined volume;
   sealing said inlet and said outlet by mounting plugs in the inlet and the outlet for transportation;
   extracting a content from said sampling membrane, wherein said content is extracted from said sampling membrane using a solvent; and
   employing a sensor unit for detecting traces of biomarkers in said content, wherein said sensor unit performs an analyzing method based on liquid chromatography mass-spectroscopy (LC/MS).

2. The method of claim 1, comprising investigating a health status of a subject based on an analysis of said traces of biomarkers.

3. The method of claim 2, wherein said investigating comprises diagnosing a medical condition of said subject, and said method further includes diagnosing said subject based on a measurement signal or result obtained from said sensor unit related to said biomarkers.

4. The method according to claim 1, including measuring a pre-defined fraction of said exhaled breath volume for determining a specific total volume of said exhaled breath passing through said sampling membrane, and when said specific total volume is determined as having passed through said sampling membrane terminating said exhalation.

5. The method according to claim 1, further comprising sending the collection device to a lab for extracting said content.

6. The method according to claim 1, including performing on-site analysis.

7. The method according to claim 1, wherein said sampling membrane comprises at least one further layer being a spunbonded carrier with a scrim weight of 10 to 20 g/m$^3$.

8. The method according to claim 1, wherein said sampling membrane has a filter surface to be passed by exhaled gas of approximately 800 mm$^2$ and a pressure drop of 36 Pa at 9.5 m/min media velocity.

9. The method according to claim 1, wherein said sampling membrane is made of a blend of acrylic fibers and polypropylene fibers.

10. The method according to claim 1, wherein
    the at least two baffles form a selective trap section that permits aerosols in said exhaled breath to pass through said tubular element.

11. The method according to claim 10, wherein each baffle comprises orifices with a size that only permit said aerosols to pass through.

12. The method according to claim 1, wherein said aerosols comprise non-volatile biomarkers in said exhaled breath; wherein said aerosols comprise non-volatile compounds of at least one biomarker in said exhaled breath and wherein said biomarker is comprised in the list comprising lipids, peptides, nucleotides, prostanoids, proteins, DNA or RNA.

13. A portable sampling device for collecting aerosols comprising biomarkers from exhaled breath of a subject for further sensor based analysis, comprising:
    a housing configured to be handheld comprising at least one inlet and at least one outlet for said exhaled breath to exit through, the housing includes a chamber made from two parts jointed together for the exhaled breath to be exhaled through and a sampling membrane comprising at least two layers, wherein at least one layer is gas permeable and another layer is an electrostatic non-woven filter, the sampling membrane being arranged transversal to a flow of exhaled breath in the chamber to collect said aerosols from the exhaled breath; plugs to be mounted in the inlet and the outlet for transportation of the device; and
    wherein said sampling membrane is a fiber based filter membrane, wherein said filter membrane comprises at least one layer of non-woven filtration media arranged transversal to the flow of exhaled breath in said chamber to collect said aerosols from said exhaled breath and wherein said sampling membrane is configured for a low pressure drop through said portable sampling device for allowing said subject to exhale through said handheld and portable device un-aided from the inlet to the outlet of said device; and wherein a content in said sampling membrane is extractable from said sampling membrane using a solvent for analysis with liquid chromatography-mass-spectroscopy;

wherein the device further comprises a detachable tubular element having a lumen in flow connection with the inlet to the chamber; wherein the tubular element is formed by two opposite parts, each part having at least one baffle, which when connected comprises at least two baffles arranged on opposite sides of said lumen to provide a non-straight path through the tubular element, said baffles protrude into said lumen at a distance larger than a radius of said lumen; the device further comprises a volume measure unit for determining that a pre-defined volume of said exhaled breath has passed through said sampling membrane, wherein the volume measure unit is connected through a port in the tubular element; and wherein said volume measure unit is a non-elastic bag with a predetermined volume.

14. The device according to claim 13, wherein the tubular element comprises a mouthpiece section for said subject to exhale into, and a selective trap section in fluid communication with said mouthpiece and said inlet of said housing, said selective trap section has the non-straight path for letting primarily aerosols pass through said tubular element.

15. The device according to claim 13, wherein said sampling membrane comprises at least one further layer being a spunbonded carrier with a scrim weight of 10 to 20 g/m$^3$.

16. The device according to claim 13, wherein said sampling membrane has a filter surface to be passed by exhaled gas of approximately 800 mm$^2$ and a pressure drop of 36 Pa at 9.5 m/min media velocity.

17. The device according to claim 13, wherein said sampling membrane is made of a blend of acrylic fibers and polypropylene fibers.

18. The device according to claim 13, wherein said housing has at least two outlets.

19. The device according to claim 13, wherein each baffle defines orifices with a size that only permit said aerosols to pass through.

20. The device according to claim 13, wherein said aerosols comprise non-volatile biomarkers in said exhaled breath; wherein said aerosols comprise non-volatile compounds of at least one biomarker in said exhaled breath and wherein said biomarker is comprised in the list comprising lipids, peptides, nucleotides, prostanoids, proteins, DNA or RNA.

21. A method for non-invasive sampling of exhaled breath for diagnosis of diseases or illnesses, comprising sampling said exhaled breath using a portable sampling device as recited in claim 13.

22. A system for diagnosing a patient by detecting a presence and/or determining a quantitative amount of at least one biomarker in exhaled breath, said system comprising the device of claim 13 and a sensor unit for analyzing a sample collected from exhaled breath of a subject by means of said device, wherein said sensor unit performs an analyzing method based on liquid chromatography mass-spectroscopy (LC/MS).

23. The method according to claim 21, wherein said diseases or illnesses comprise cancer, inflammation, infection and/or oxidative stress.

* * * * *